US008850898B2

(12) United States Patent
Johnsen

(10) Patent No.: US 8,850,898 B2
(45) Date of Patent: Oct. 7, 2014

(54) TEST FIXTURE FOR STRIP SAMPLES

(75) Inventor: David J. Johnsen, Plymouth, MN (US)

(73) Assignee: ADC Telecommunications, Inc., Berwyn, PA (US)

( * ) Notice: Subject to any disclaimer, the term of this patent is extended or adjusted under 35 U.S.C. 154(b) by 45 days.

(21) Appl. No.: 13/605,543

(22) Filed: Sep. 6, 2012

(65) Prior Publication Data

US 2013/0145859 A1    Jun. 13, 2013

Related U.S. Application Data

(60) Provisional application No. 61/531,340, filed on Sep. 6, 2011.

(51) Int. Cl.
*G01N 3/20* (2006.01)
*G01N 3/04* (2006.01)
*G01N 3/02* (2006.01)

(52) U.S. Cl.
CPC .......... *G01N 3/02* (2013.01); *G01N 2203/0282* (2013.01); *G01N 3/04* (2013.01); *G01N 2203/0005* (2013.01); *G01N 2203/0206* (2013.01); *G01N 2203/0476* (2013.01); *G01N 2203/0023* (2013.01)
USPC ........................................ 73/849; 73/862.637

(58) Field of Classification Search
USPC ....................... 73/778, 849, 862.637, 862.451
See application file for complete search history.

(56) References Cited

U.S. PATENT DOCUMENTS

| | | | |
|---|---|---|---|
| 2,032,989 A | 3/1936 | Kenney et al. | |
| 3,194,063 A | 7/1965 | McKean | |
| 3,500,679 A | 3/1970 | Smith | |
| 4,625,563 A | 12/1986 | Dawson et al. | |
| 4,991,446 A * | 2/1991 | Bechtel | 73/849 |
| 5,178,017 A | 1/1993 | Dinzburg | |
| 5,804,738 A * | 9/1998 | Bach et al. | 73/849 |
| 5,951,790 A * | 9/1999 | Mannava et al. | 148/510 |
| 6,053,052 A * | 4/2000 | Starostovic | 73/851 |
| 6,055,867 A | 5/2000 | Dunne et al. | |
| 7,302,860 B1 * | 12/2007 | Uhlik et al. | 73/853 |
| 7,974,803 B2 * | 7/2011 | Logan et al. | 702/88 |
| 2002/0059834 A1 * | 5/2002 | Onoue | 73/812 |

OTHER PUBLICATIONS

GR-771-CORE Generic Requirements for Fiber Optic Splice Closures, Issue 2, dated Jul. 2008, 1 pg.
ADC Telecommunications, Inc., 3 Point Bend Fixture, admitted as prior art as of the filing date of the provisional application Sep. 6, 2011, 1 pg.
TE Connectivity, 3 Point Bend Fixture, admitted as prior art as of the filing date of the provisional application Sep. 6, 2011, 3 pgs.

* cited by examiner

*Primary Examiner* — Max Noori
(74) *Attorney, Agent, or Firm* — Merchant & Gould P.C.

(57) ABSTRACT

A test fixture for applying a prescribed displacement to a material includes a first and a second portion, a first and a second adjustable pin, and an actuator. The first portion includes a first pin that to engages the material at a first location on the material. A second pin is engages the material at a second location on the material. A third pin engages the material at a third location on the material. The first adjustable pin holds the material against the second pin at the second location. The second adjustable pin holds the material against the third pin at the third location. The actuator is adapted to configure a relative position between the first pin and the second and third pins.

37 Claims, 12 Drawing Sheets

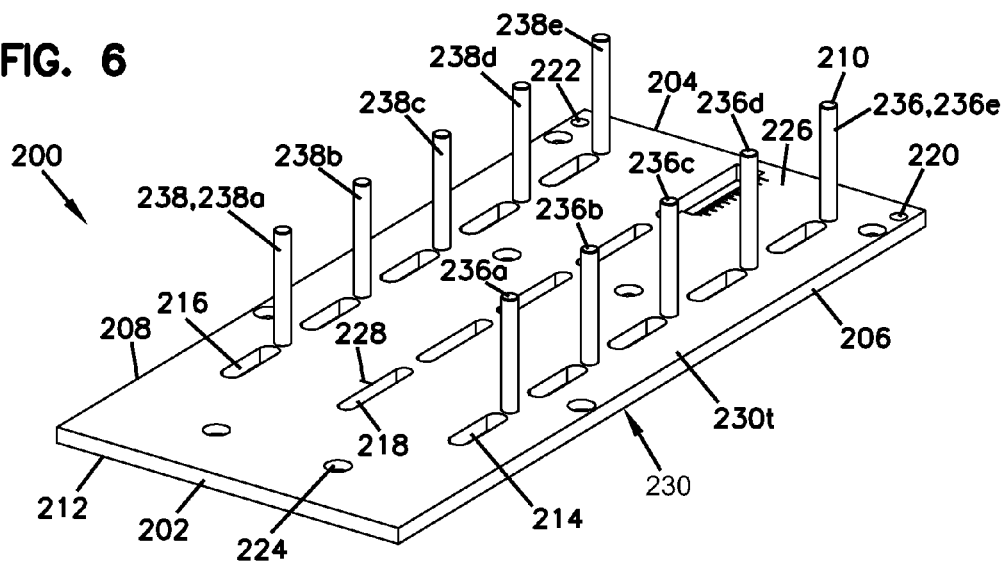
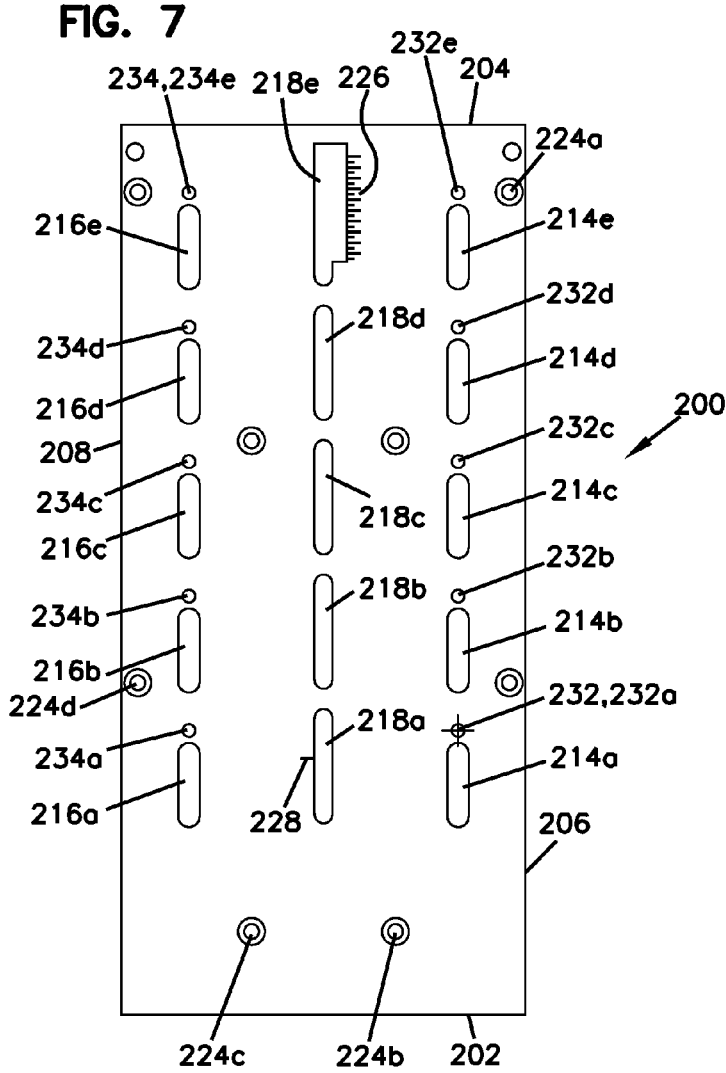
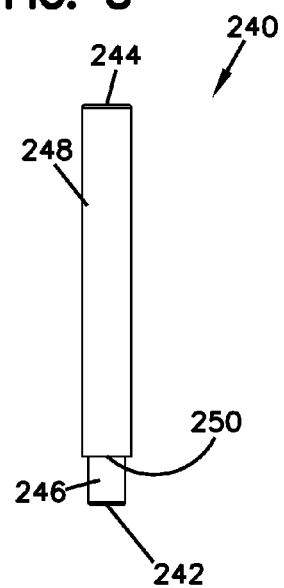

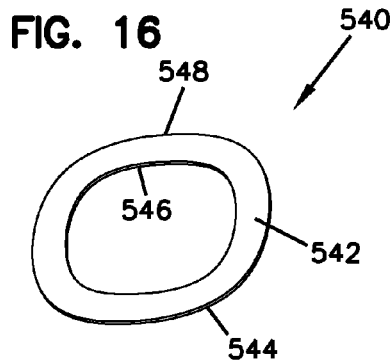
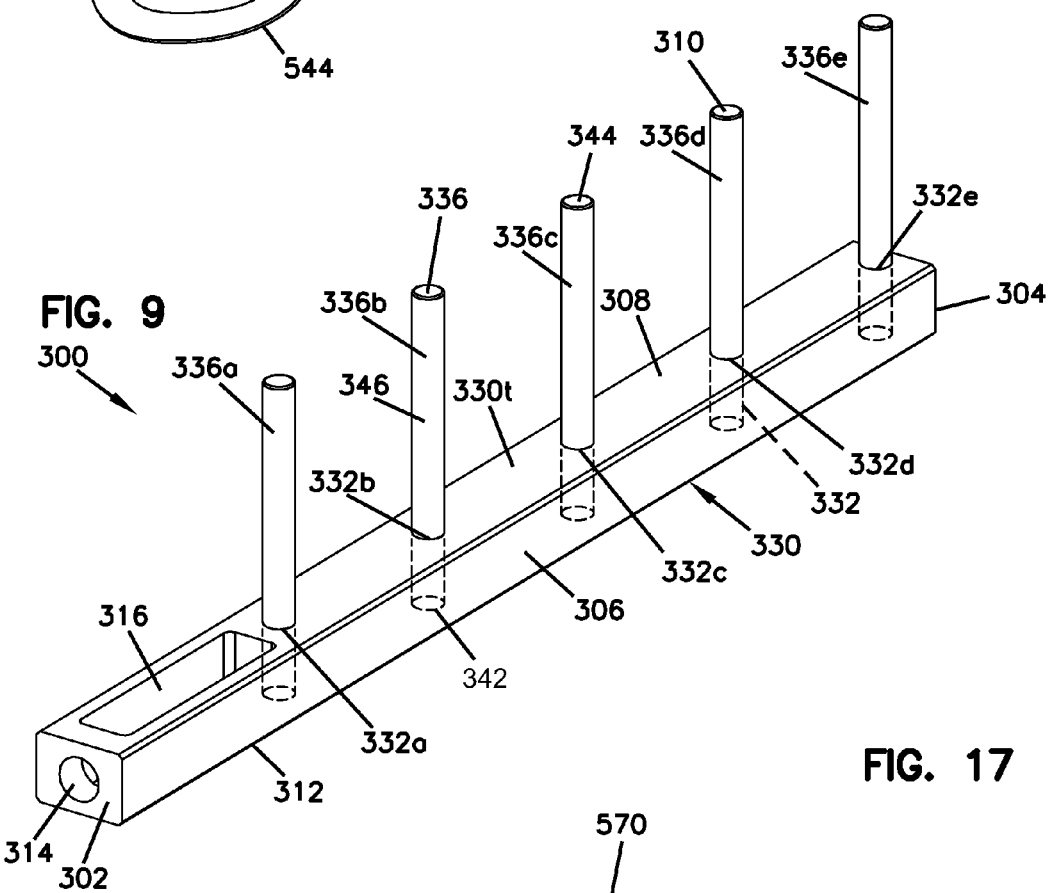
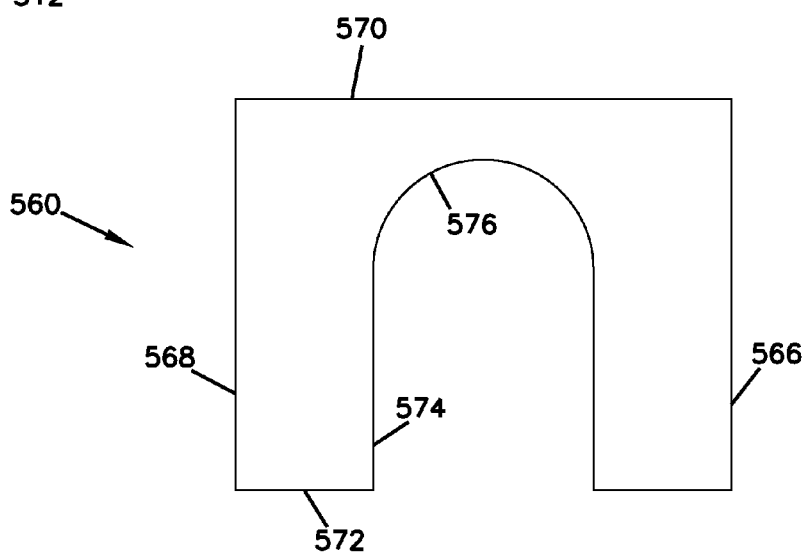

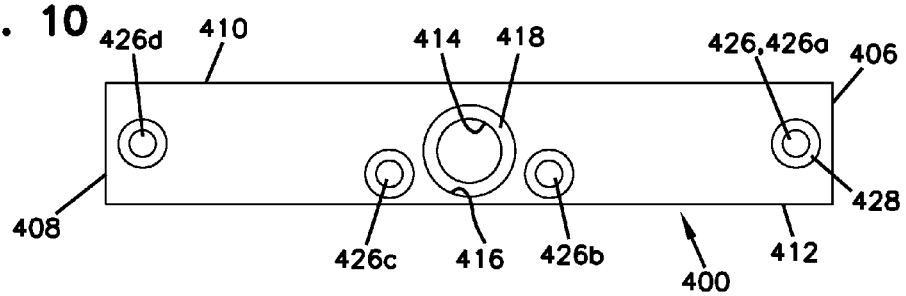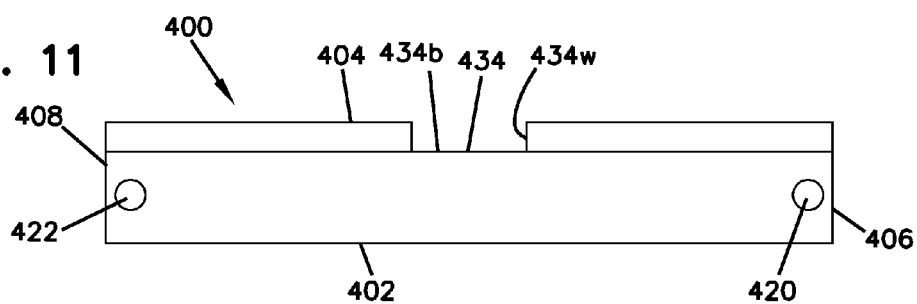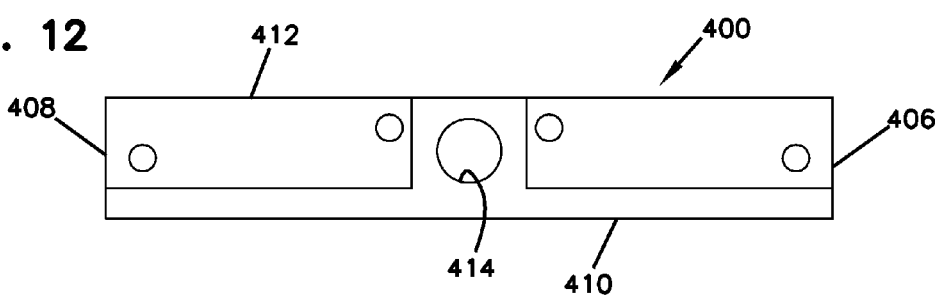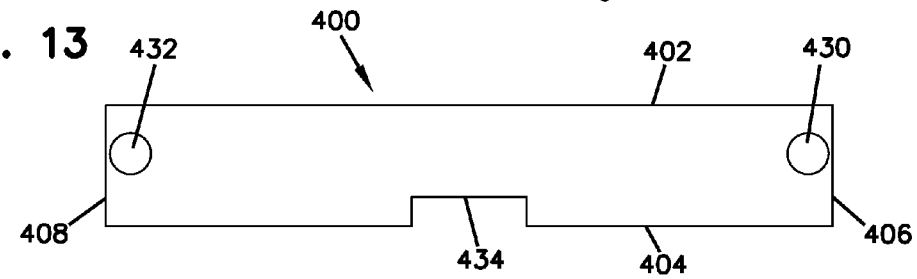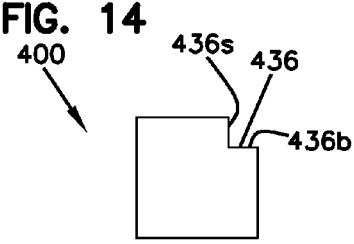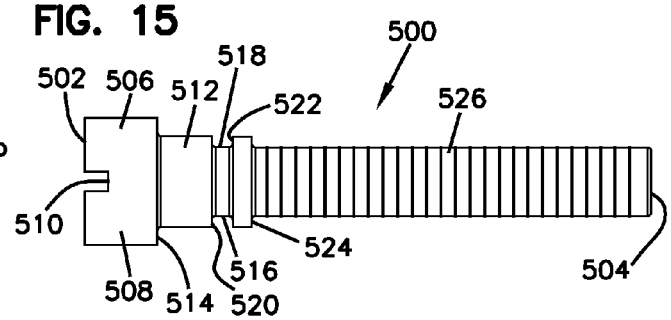

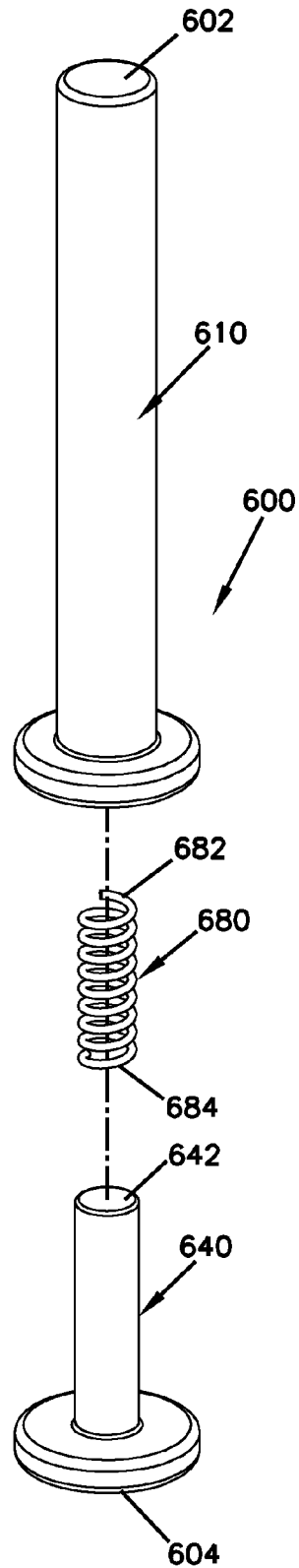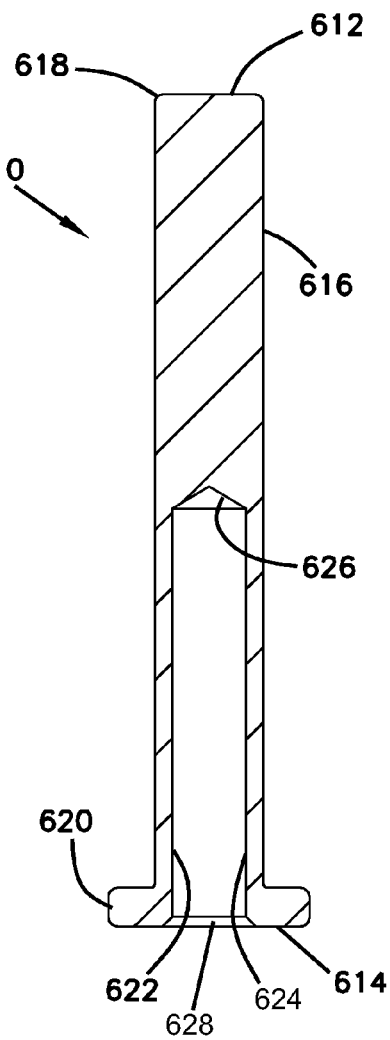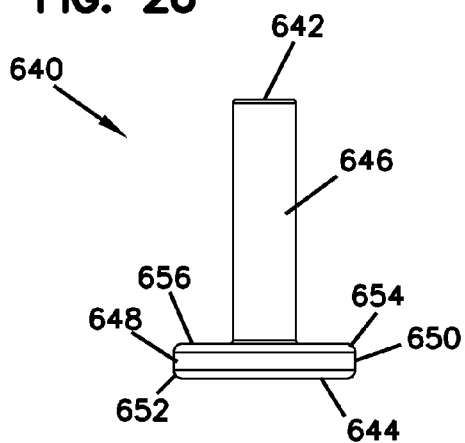

FIG. 21
FIG. 22
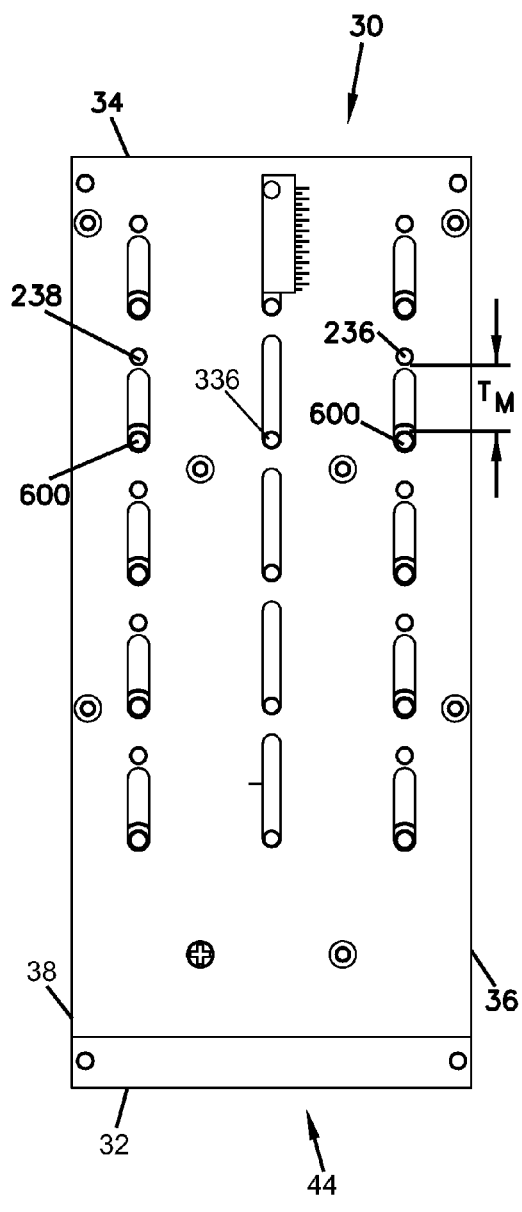
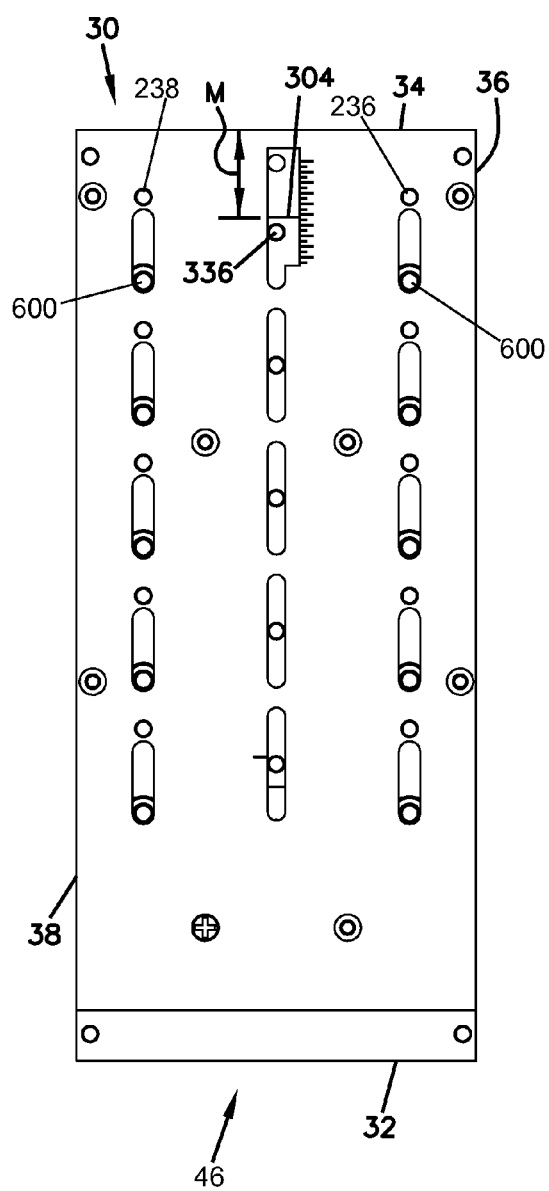

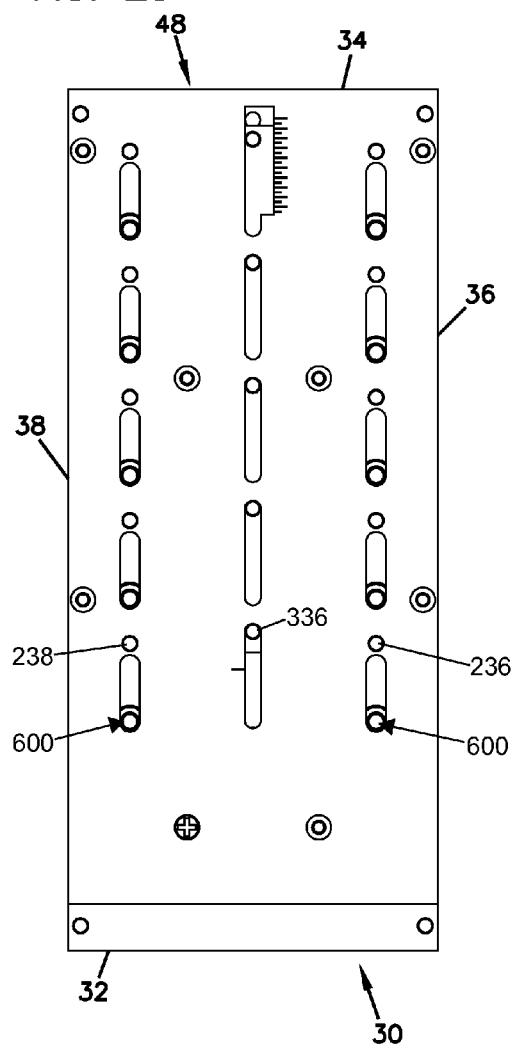
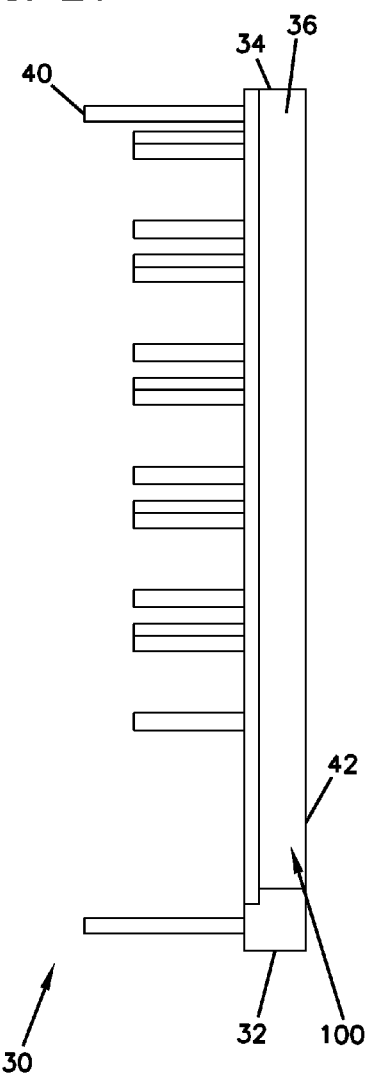
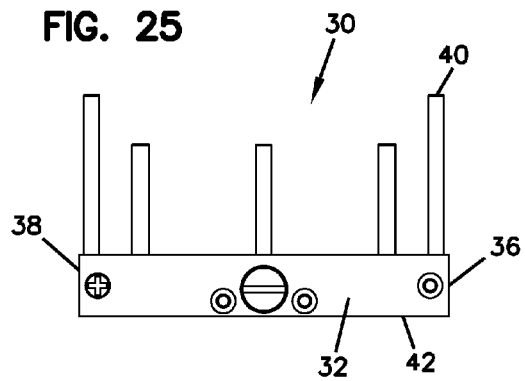

TEST FIXTURE FOR STRIP SAMPLES

CROSS-REFERENCE TO RELATED APPLICATION

This application claims the benefit of U.S. Provisional Patent Application Ser. No. 61/531,340, filed Sep. 6, 2011, which application is hereby incorporated by reference in its entirety.

FIELD

The inventive aspects of this disclosure pertain to devices and methods for testing materials.

BACKGROUND

Material tests and standards have been devised to qualify materials for use in particular applications. These tests include strength tests, deflections tests, chemical resistance tests, fatigue tests, etc. Certain of these tests may test combinations of properties and/or subject a test specimen to several test conditions simultaneously (e.g., a deflection test combined with a chemical resistance test). There is a need for test fixtures to efficiently perform tests on a range of materials.

SUMMARY

An aspect of the present disclosure relates to a test fixture for applying a prescribed displacement to a material. The test fixture includes a first portion, a second portion, and an actuator. The first portion includes a first material engaging feature and a first support. The first material engaging feature includes a supported end mounted to the first support and a free end spaced from the supported end of the first material engaging feature. The first material engaging feature is adapted to engage the material between the supported end and the free end of the first material engaging feature at a first location on the material. The second portion includes a second material engaging feature, a third material engaging feature, and a second support. The second and the third material engaging features each have a supported end mounted to the second support. The second and the third material engaging features are spaced from each other by a distance. The second and the third material engaging features each include a free end spaced from the supported ends of the second and the third material engaging features. The second material engaging feature is adapted to engage the material between the supported end and the free end of the second material engaging feature at a second location on the material. The third material engaging feature is adapted to engage the material between the supported end and the free end of the third material engaging feature at a third location on the material. The actuator is operably connected between the first support of the first portion and the second support of the second portion. The actuator is adapted to configure a relative position between the first material engaging feature and the second and third material engaging features.

Another aspect of the present disclosure relates to a test fixture for simultaneously applying prescribed displacements to a plurality of test specimens. The test fixture includes a first portion, a second portion, and an actuator. The first portion includes a plurality of material engaging features. The material engaging features of the first portion are each adapted to engage one of the test specimens at a first location on the test specimen. The second portion includes a plurality of pairs of material engaging features. The pairs of material engaging features of the second portion are each adapted to engage one of the test specimens at a second location and a third location on the test specimen. One of the pair of material engaging features is adapted to engage the test specimens at the second locations, and another of the pair of material engaging features is adapted to engage the test specimens at the third locations. The actuator is operably connected between the first portion and the second portion. The actuator is adapted to configure a relative position between the material engaging features of the first portion and the pairs of material engaging features of the second portion.

Still another aspect of the present disclosure relates to a test fixture for applying a prescribed displacement to a material. The test fixture includes a first portion, a second portion, a first adjustable material support feature, a second adjustable material support feature, and an actuator. The first portion includes a first pin. The first pin is adapted to engage the material at a first location on the material. The second portion includes a second pin and a third pin. The second and the third pins are spaced from each other by a distance. The second pin is adapted to engage the material at a second location on the material. The third pin is adapted to engage the material at a third location on the material. The first adjustable material support feature is adapted to hold the material against the second pin at the second location on the material. The second adjustable material support feature is adapted to hold the material against the third pin at the third location on the material. The actuator is operably connected between the first portion and the second portion. The actuator is adapted to configure a relative position between the first pin and the second and third pins.

A variety of additional aspects will be set forth in the description that follows. These aspects can relate to individual features and to combinations of features. It is to be understood that both the foregoing general description and the following detailed description are exemplary and explanatory only and are not restrictive of the broad concepts upon which the embodiments disclosed herein are based.

BRIEF DESCRIPTION OF THE DRAWINGS

FIG. 6 is a perspective view of a stationary material engaging portion of the test fixture of FIG. 1 including a plate and a plurality of material engaging pins;

FIG. 7 is a top plan view of the plate of the stationary material engaging portion of FIG. 6;

FIG. 8 is an elevation view of the material engaging pin of the stationary material engaging portion of FIG. 6;

FIG. 9 is a perspective view of a moveable material engaging portion of the test fixture of FIG. 1;

FIG. 10 is an end elevation view of an end-piece of the test fixture of FIG. 1;

FIG. 11 is a top plan view of the end piece of FIG. 10;

FIG. 12 is an opposite end elevation view of the end piece of FIG. 10;

FIG. 13 is a bottom plan view of the end piece of FIG. 10;

FIG. 14 is a side elevation view of the end piece of FIG. 10;

FIG. 15 is a side elevation view of an actuating screw of the test fixture of FIG. 1;

FIG. 16 is a perspective view of a compression washer of the test fixture of FIG. 1;

FIG. 17 is an end elevation view of a retaining member of the test fixture of FIG. 1;

FIG. 18 is an exploded perspective view of a support pin assembly of the test fixture of FIG. 1;

FIG. 19 is a cross-sectional side elevation view of a pin of the support pin assembly of FIG. 18;

FIG. 20 is a side elevation view of a plunger of the support pin assembly of FIG. 18;

FIG. 21 is a top plan view of the test fixture of FIG. 1 in an un-actuated configuration;

FIG. 22 is a top plan view of the test fixture of FIG. 1 in a partially actuated configuration;

FIG. 23 is a top plan view of the test fixture of FIG. 1 in a fully actuated configuration;

FIG. 24 is a side elevation view of the test fixture of FIG. 1 in the fully actuated configuration of FIG. 23;

FIG. 25 is an end elevation view of the test fixture of FIG. 1;

DETAILED DESCRIPTION

Reference will now be made in detail to the exemplary aspects of the present disclosure that are illustrated in the accompanying drawings. Wherever possible, the same reference numbers will be used throughout the drawings to refer to the same or like structure.

Figure 26:
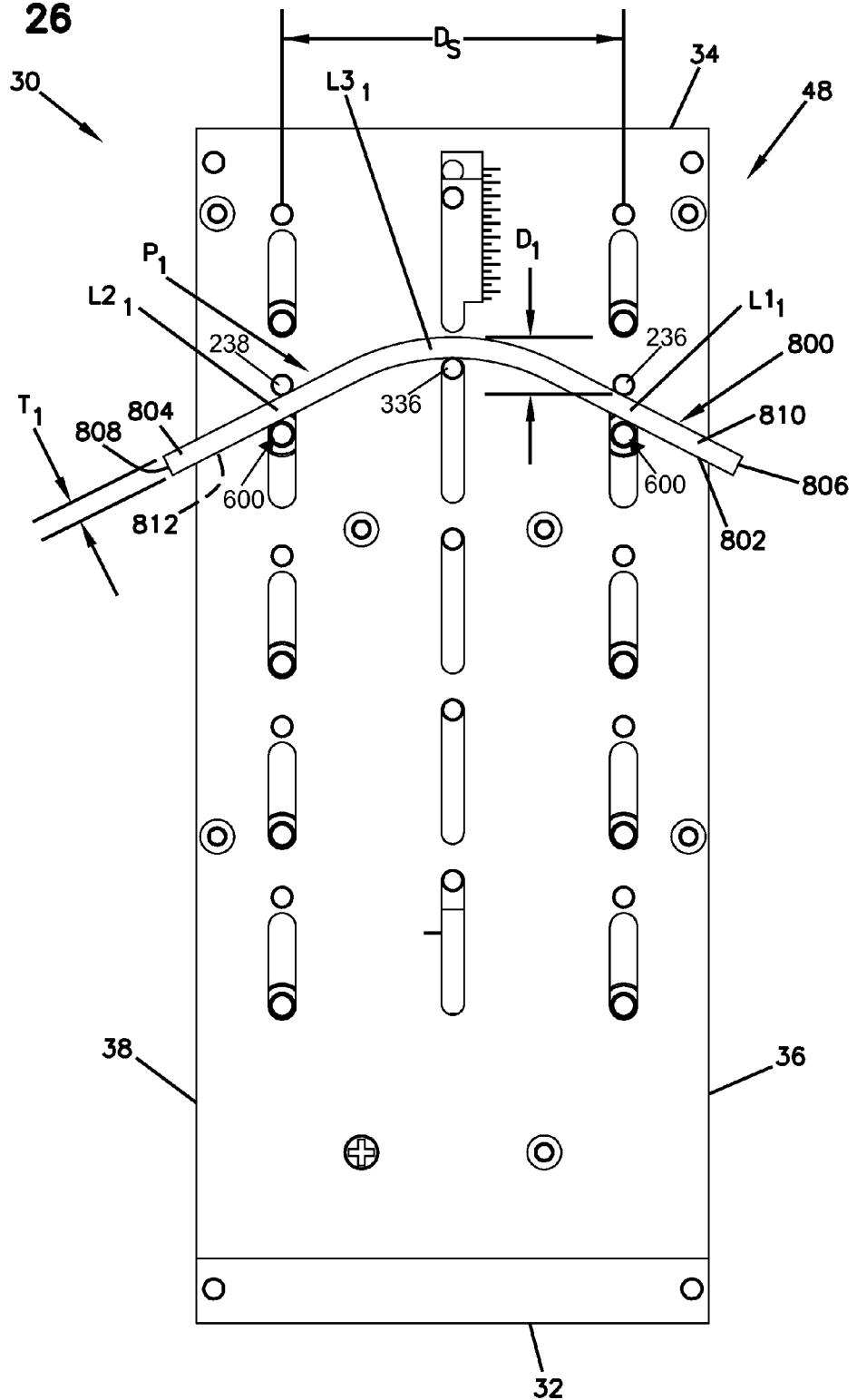
FIG. 26 is a top plan view of the test fixture of FIG. 1 in the fully actuated configuration of FIG. 23 with a first test specimen loaded therein.
Figure 27:
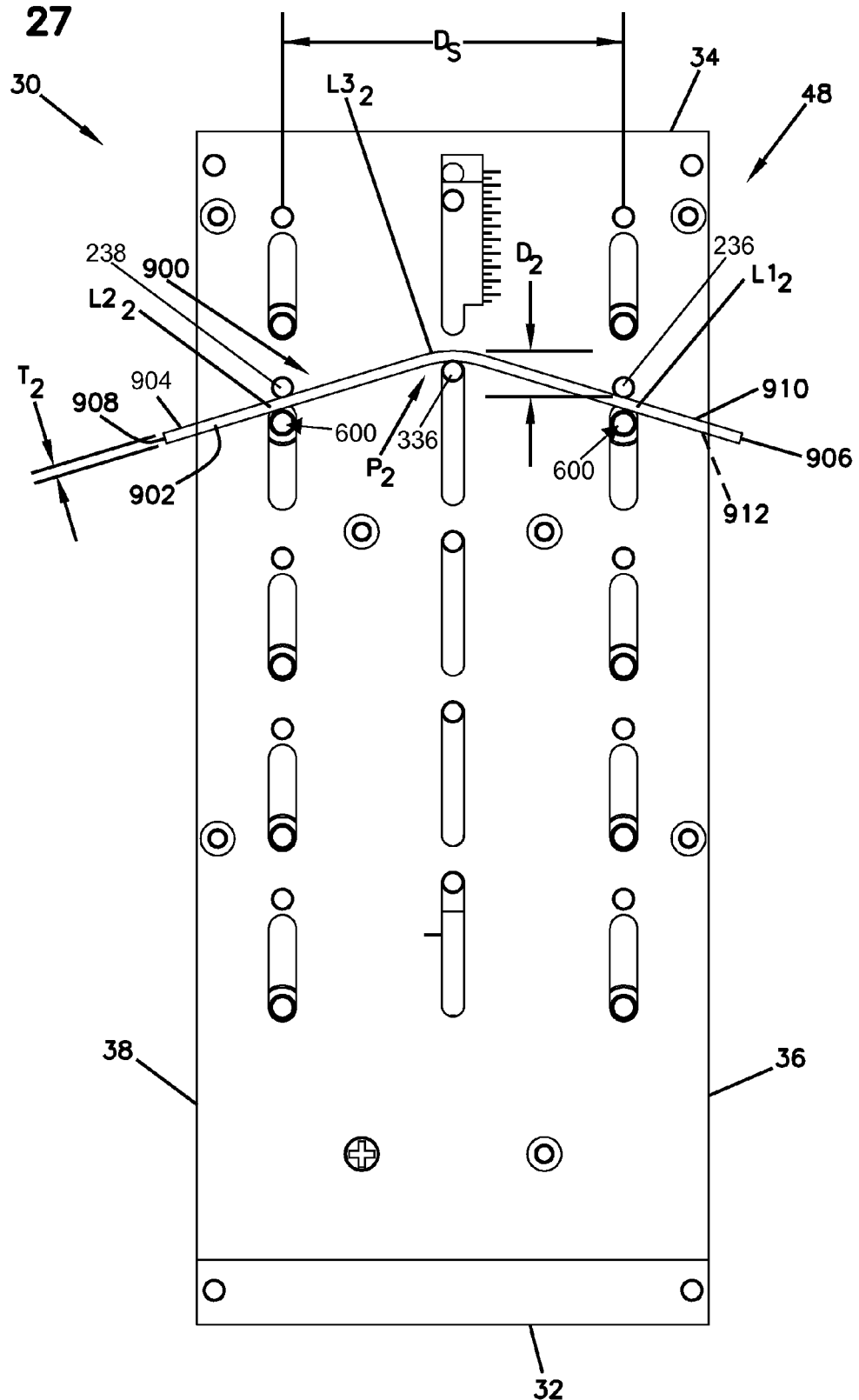
FIG. 27 is a top plan view of the test fixture of FIG. 1 in the fully actuated configuration of FIG. 23 with a second test specimen loaded therein.
Figure 28:
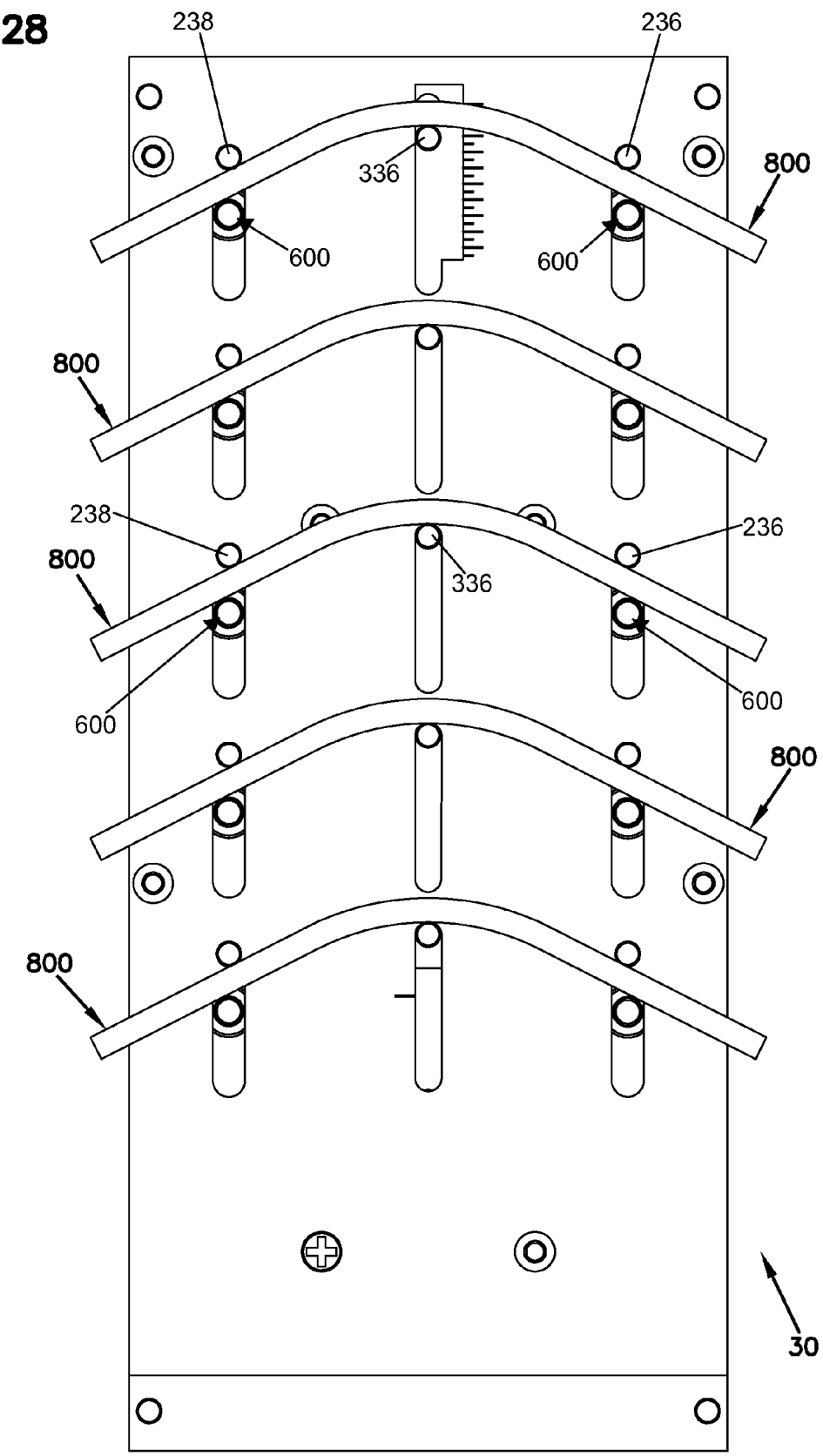
FIG. 28 is a top plan view of the test fixture of FIG. 1 in the fully actuated configuration of FIG. 23 with a set of the first test specimens of FIG. 26 loaded therein.

The present disclosure concerns test fixtures for qualifying material for a given application and/or determining whether a material sample meets a given specification. In particular, an example test fixture 30 is disclosed that tests various materials under various bending conditions. The various materials can vary in thickness, stiffness (e.g., modulus of elasticity), strength, creep, chemical resistance, etc. The example test fixture 30 can impose various deformation profiles on the various material samples (e.g., test specimens). In the depicted use of the test fixture 30, as illustrated at FIGS. 26-28, the test fixture 30 constrains material samples 800 or 900 at two locations $L1_{1,2}$ and $L2_{1,2}$, respectively, that are spaced apart from each other by, or approximately by, a predetermined distance $D_S$. The test fixture 30 can displace the material samples 800, 900 at a third location $L3_{1,2}$, between the two constrained locations $L1_{1,2}$, $L2_{1,2}$, by a predetermined distance $D_{1,2}$. As depicted, the material samples 800, 900 are initially straight and are deformed to deformation profiles $P_{1,2}$ by the test fixture 30.

Figure 1:
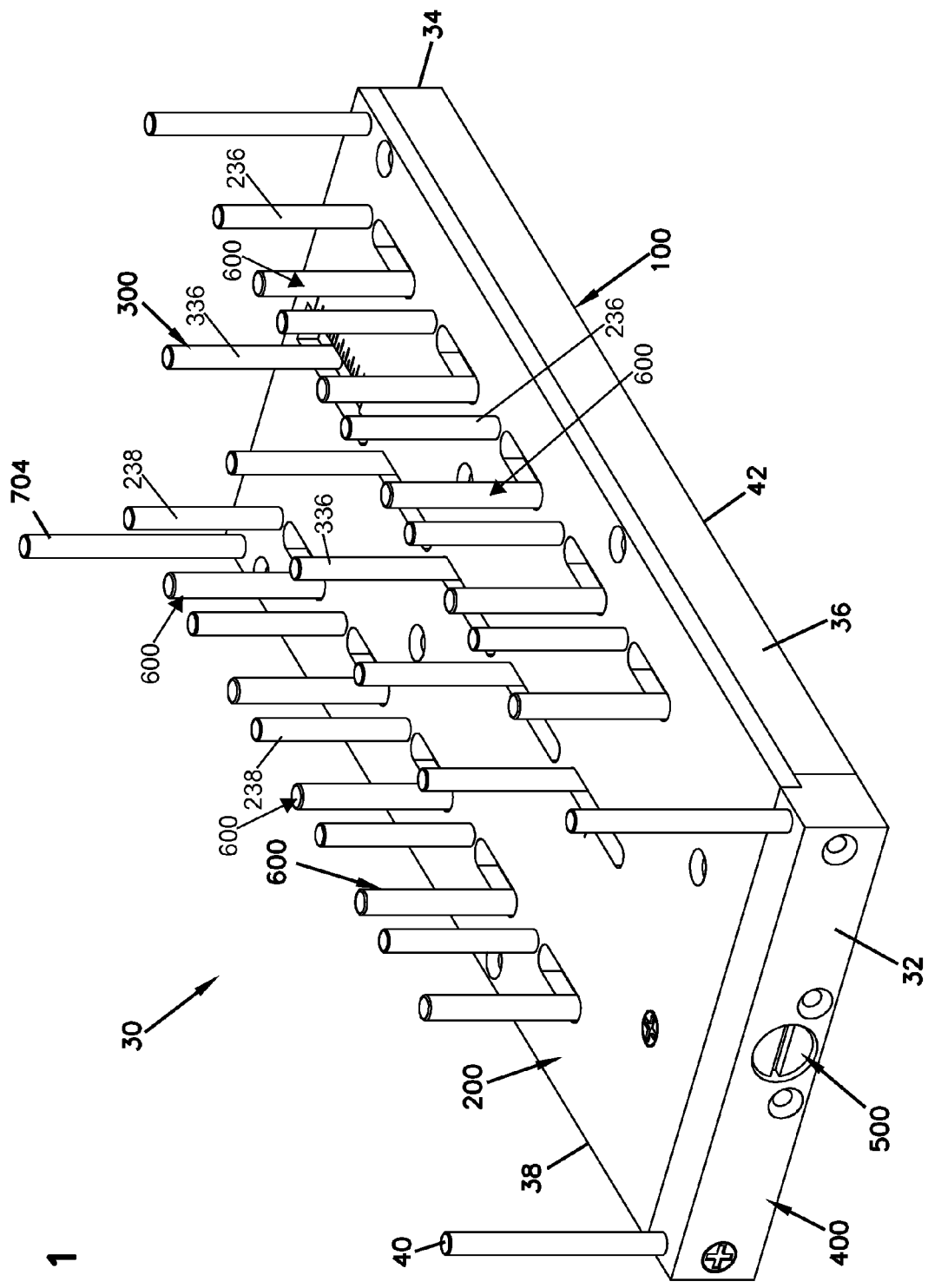
FIG. 1 is a perspective view of a test fixture in accordance with the principles of the present disclosure.
Figure 2:
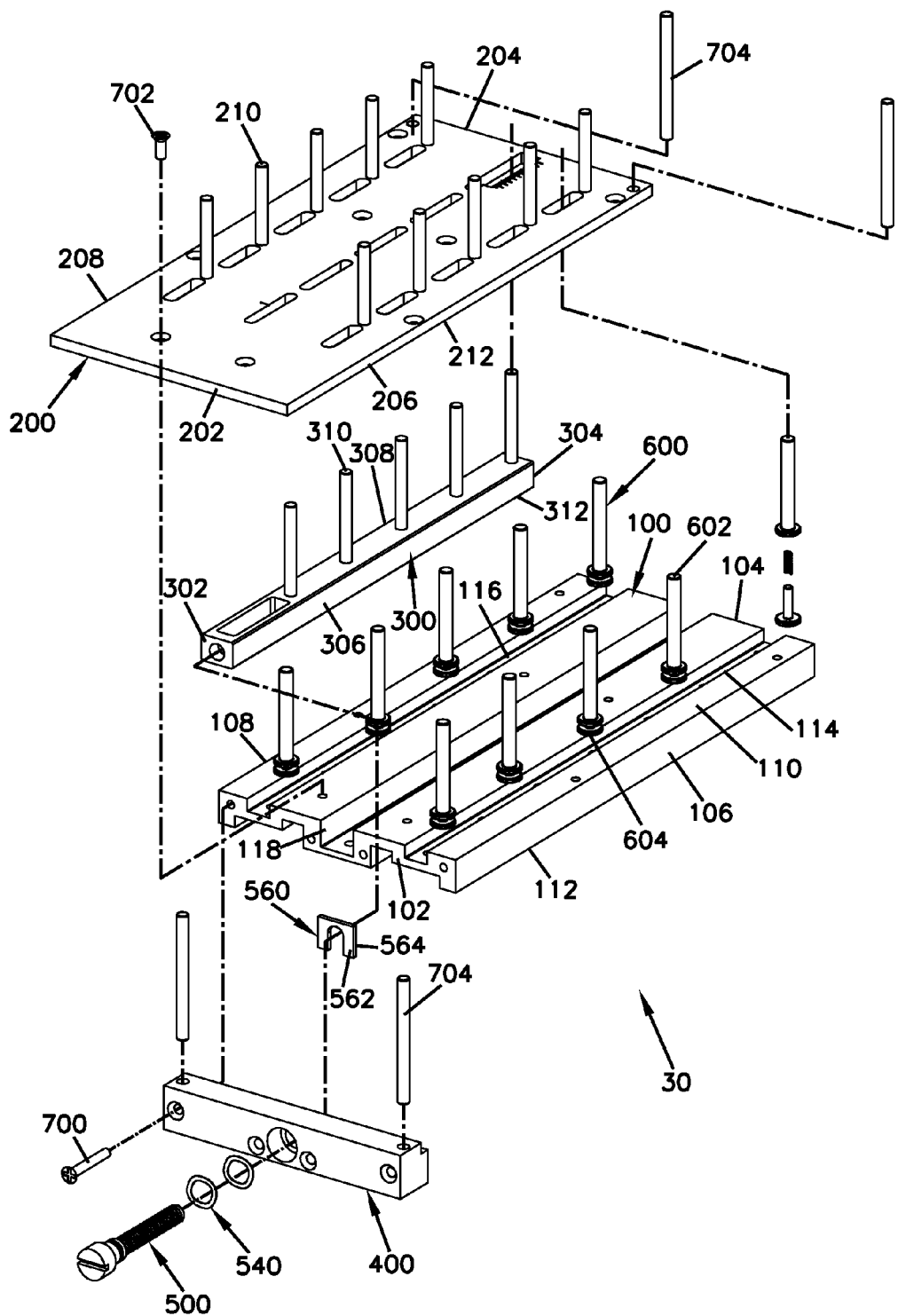
FIG. 2 is an exploded perspective view of the test fixture of FIG. 1.

Referring now to FIGS. 1 and 2, the test fixture 30 will be described in detail. The test fixture 30 extends between a first end 32 and a second end 34. The test fixture 30 also includes a first side 36, a second side 38, a top 40, and a bottom 42. The test fixture 30 can be configured in multiple configurations. FIG. 21 illustrates a first configuration 44 of the test fixture 30. FIG. 23 illustrates a second configuration 48 of the test fixture 30. As depicted, the first configuration 44 and the second configuration 48 position the test fixture 30 at opposite ends of a range of available configurations. FIG. 22 illustrates an intermediate configuration 46 between the first configuration 44 and the second configuration 48. The test fixture 30 is configurable to other intermediate configurations between the first configuration 44 and the second configuration 48. An intermediate configuration (e.g., the intermediate configuration 46) can be chosen to meet the requirements of a material test performed by the test fixture 30. The first configuration 44 or the second configuration 48 can also be chosen to meet the requirements of a material test performed by the test fixture 30.

The test fixture 30 includes a base 100, a stationary portion 200, a moveable portion 300, an adjustment bracket 400, an actuator 500, a preloading member 540, a keeper 560, a plurality of support pin assemblies 600, and a plurality of stacking pins 704. As depicted, a material sample or material samples are held between the stationary portion 200 and the moveable portion 300. The actuator 500 moves the moveable portion 300 relative to the stationary portion 200. By moving the moveable portion 300 relative to the stationary portion 200, the material sample or the material samples are deformed (e.g., according to a predetermined requirement and/or to a predetermined deformation profile).

Figure 3:
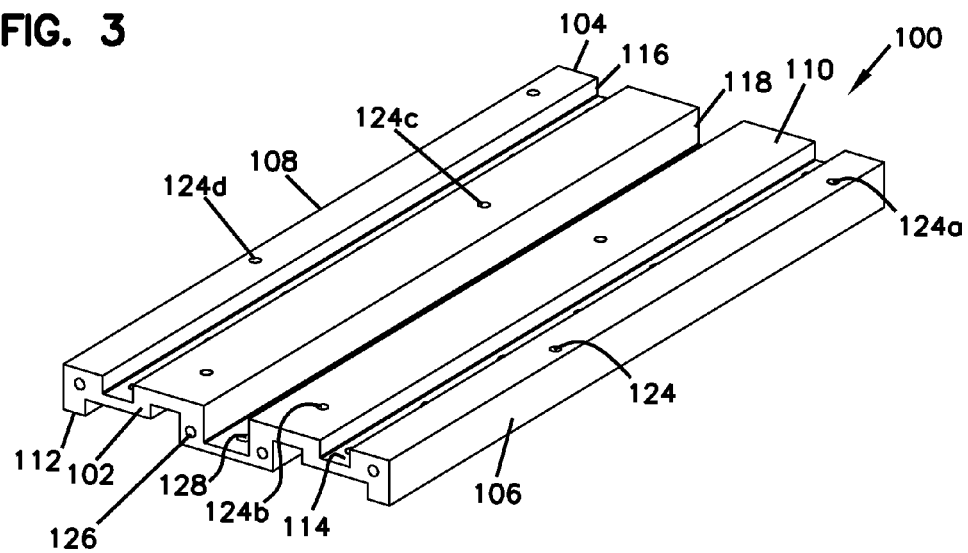
FIG. 3 is a perspective view of a base of the test fixture of FIG. 1.
Figure 4:
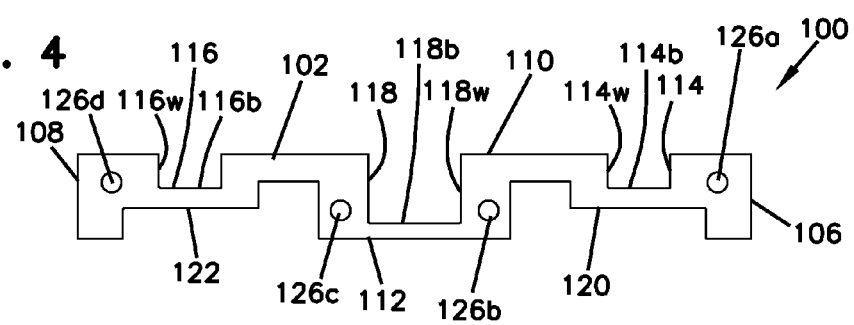
FIG. 4 is an end elevation view of the base of FIG. 3.
Figure 5:
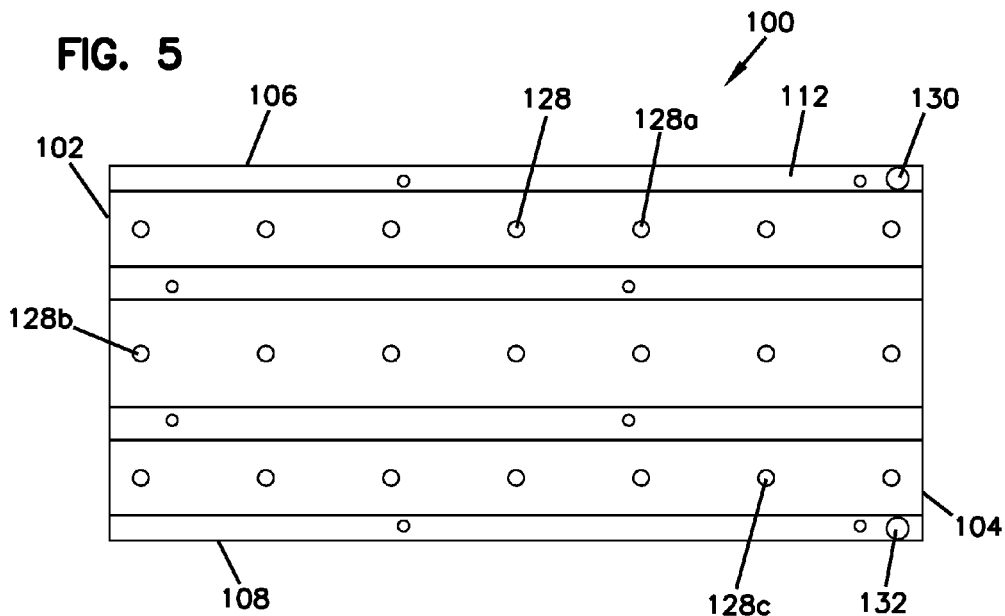
FIG. 5 is a bottom plan view of the base of FIG. 3.

Turning now to FIGS. 3-5, the base 100 will be described in detail. The base 100 extends between a first end 102 and a second end 104. As depicted, the second end 104 of the base 100 generally corresponds to the second end 34 of the test fixture 30. The base 100 further includes a first side 106, a second side 108, a top 110, and a bottom 112. As depicted, the first side 106 of the base 100 generally corresponds to the first side 36 of the test fixture 30, the second side 108 of the base 100 generally corresponds to the second side 38 of the test fixture 30, and the bottom 112 of the base 100 generally corresponds to the bottom 42 of the test fixture 30.

A first channel 114 of the base 100 extends between the first end 102 and the second end 104. Likewise, a second channel 116 extends between the first end 102 and the second end 104. The first channel 114 includes a bottom 114b and a pair of walls 114w adjacent each side of the bottom 114b. Likewise, the second channel 116 includes a bottom 116b and a pair of walls 116w adjacent each side of the bottom 116b. The base 100 further includes a channel 118 that extends between the first end 102 and the second end 104. As depicted, the channel 118 is a center channel. The channel 118 is positioned between the channels 114 and 116. The channel 118 includes a bottom 118b and a pair of walls 118w adjacent each side of the bottom 118b. As depicted, the channels 114, 116, 118 open toward the top 110 of the base 100. The base 100 further includes a first relief 120 and a second relief 122. As depicted, the reliefs 120, 122 open toward the bottom 112.

The base 100 further includes a series of holes 124 (e.g., top holes). As depicted, the holes 124 open toward the top 110 of the base 100. The holes 124 are arranged in rows. A first row of holes 124a is positioned between the first side 106 and the first channel 114. A second row of holes 124b is positioned between the first channel 114 and the channel 118. A third row of holes 124c is positioned between the channel 118 and the second channel 116. A fourth row of holes 124d is positioned between the second channel 116 and the second side 108.

The base 100 further includes a series of holes 126 (e.g., end holes). As depicted, the holes 126 generally open toward the first end 102. A first hole 126a is positioned between the first side 106 and the first channel 114. A second hole 126b is positioned between the first channel 114 and the channel 118. A third hole 126c is positioned between the channel 118 and the second channel 116. A fourth hole 126d is positioned between the second channel 116 and the second side 108. As depicted, the holes 124, 126 are threaded holes that are used for fastening other components to the base 100.

The base 100 further includes holes 128 at the channels 114, 116, 118. In particular, a first set of holes 128a is positioned at the bottom 114b of the first channel 114. Likewise, a second set of holes 128c is positioned at a bottom 116b of the second channel 116. Likewise, a third set of holes 128b is positioned at the bottom 118b of the channel 118. As depicted, the holes 128 provide openings between the top 110 and the bottom 112 of the base 100. The holes 128 may be used as drain holes to drain fluids from the channels 114, 116, 118.

The base 100 further includes a pair of stacking holes 130. The stacking holes 130 are located adjacent the second end 104 of the base 100 and are also located adjacent the first side 106 and the second side 108, respectively. Each of the stacking holes 130 includes a hole bottom 132.

Turning now to FIGS. 6 and 7, the stationary portion 200 of the test fixture 30 will be described in detail. The stationary portion 200 extends from a first end 202 to a second end 204. As depicted, the second end 204 generally corresponds to the second end 34 of the test fixture 30. The stationary portion 200 further includes a first side 206, a second side 208, a top 210, and a bottom 212. As depicted, the first side 206 generally corresponds to the first side 36 of the test fixture 30, the second side 208 generally corresponds to the second side 38 of the test fixture 30, and the bottom 212 of the stationary portion 200 generally abuts the top 110 of the base 100.

The stationary portion 200 includes a first series of slots 214. The first slots 214 are generally aligned and extend in a direction between the first and the second ends 202, 204. The first slots 214 include slots 214a, 214b, 214c, 214d, and 214e. The first slots 214a-e are positioned in a row with the slot 214a nearest the first end 202 and the slot 214e nearest the second end 204. The stationary portion 200 further includes a second series of slots 216. The second slots 216 are generally aligned and extend in the direction between the first and the second ends 202, 204. The second slots 216 include slots 216a, 216b, 216c, 216d, and 216e. The second slots 216a-e are positioned in a row with the slot 216a nearest the first end 202 and the slot 216e nearest the second end 204. The stationary portion 200 further includes a third series of slots 218. The third slots 218 are generally aligned and extend in the direction between the first and the second ends 202, 204. The third slots 218 include slots 218a, 218b, 218c, 218d, and 218e. The third slots 218a-e are positioned in a row with the slot 218a nearest the first end 202 and the slot 218e nearest the second end 204. The first slots 214 are positioned adjacent the first side 206. The second slots 216 are positioned adjacent the second side 208 of the stationary platform 200. The third slots 218 are positioned between the slots 214 and the slots 216. The first slots 214 generally correspond with the first channel 114 of the base 100. Likewise, the second slots 216 generally correspond with the second channel 116 of the base 100. Likewise, the third slots 218 of the stationary portion 200 generally correspond with the channel 118 of the base 100.

The stationary portion 200 further includes a first stacking pin hole 220 and a second stacking pin hole 222. The first stacking pin hole 220 is positioned adjacent the first side 206 and also adjacent the second end 204. The second stacking pin hole 222 is positioned adjacent the second side 208 and positioned adjacent the second end 204.

The stationary portion 200 further includes a series of mounting holes 224. The mounting holes 224 are arranged in a series of rows. A first series of mounting holes 224a is positioned between the first slots 214 and the first side 206. The mounting holes 224a generally correspond with the holes 124a of the base 100. A second series of mounting holes 224b is positioned between the first slots 214 and the third slots 218. The mounting holes 224b generally correspond with the holes 124b of the base 100. A third series of mounting holes 224c is positioned between the third slots 218 and the second slots 216. The mounting holes 224c generally correspond with the holes 124c of the base 100. A fourth series of mounting holes 224d is positioned between the second slots 216 and the second side 208 of the stationary portion 200.

In the depicted embodiment, a scale 226 is positioned adjacent the slot 218e, as shown at FIG. 7. As depicted, an indicator mark 228 is positioned adjacent the slot 218a, as illustrated at FIG. 7.

As depicted, the slots 214, 216, 218 and the holes 224 of the stationary portion 200 are included in a plate 230 of the stationary portion 200. The plate 230 generally extends between the first end 202 and the second end 204. The plate 230 also extends between the first side 206 and the second side 208 of the stationary portion 200. The plate 230 also extends from the bottom 212 of the stationary portion 200 to a top surface 230t of the plate 230.

The stationary portion 200 further includes a first series of pin holes 232 and a second series of pin holes 234. As depicted, the first and the second series of pin holes 232, 234 are included in the plate 230. The first series of the pin holes 232 includes a first pin hole 232a, a second pin hole 232b, a third pin hole 232c, a fourth pin hole 232d, and a fifth pin hole 232e. The pin holes 232 are generally aligned with the slots 214. The pin hole 232a is positioned between the slots 214a and 214b. The pin hole 232b is positioned between the slots 214b and 214c. The pin hole 232c is positioned between the slots 214c and 214d. The pin hole 232d is positioned between the slots 214d and 214e. And, the pin hole 232e is positioned between the slot 214e and the second end 204 of the stationary portion 200. The second series of the pin holes 234 includes a first pin hole 234a, a second pin hole 234b, a third pin hole 234c, a fourth pin hole 234d, and a fifth pin hole 234e. The pin holes 234 are generally aligned with the slots 216. The pin hole 234a is positioned between the slots 216a and 216b. The pin hole 234b is positioned between the slots 216b and 216c. The pin hole 234c is positioned between the slots 216c and 216d. The pin hole 234d is positioned between the slots 216d and 216e. And, the pin hole 234e is positioned between the slot 216e and the second end 204 of the stationary portion 200.

The stationary portion 200 includes a first series of fixed pins 236 and a second series of fixed pins 238. As depicted, the first series of fixed pins 236 includes a first pin 236a, a second pin 236b, a third pin 236c, a fourth pin 236d, and a fifth pin 236e. The first series of the fixed pins 236 are positioned within the corresponding pin holes 232. As depicted, the second series of the fixed pins 238 includes a first pin 238a, a second pin 238b, a third pin 238c, a fourth pin 238d, and a fifth pin 238e. The second series of the fixed pins 238 are positioned within the corresponding pin holes 234. A pin 240 is illustrated at FIG. 8. The pin 240 can be used as the fixed pins 236a-e and the fixed pins 238a-e. The pin 240 extends between a first end 242 and a second end 244. The pin 240 includes a first diameter 246 adjacent the first end 242. As illustrated, the first diameter 246 is chamfered at the first end 242. The pin 240 also includes a second diameter 248 adjacent the second end 244. As depicted, the second diameter 248 is chamfered at the second end 244. As depicted, the first diameter 246 and the second diameter 248 are concentric with each other. A shoulder 250 is positioned between the first diameter 246 and the second diameter 248. In a preferred embodiment, the pin holes 232, 234 are sized for a press fit (i.e., an interference fit) with the first diameter 246 of the pin 240. As depicted, the first diameter 246 is inserted into the pin holes 232, 234 until the shoulder 250 abuts the top 230t of the plate 230.

Turning now to FIG. 9, the moveable portion 300 will be described in detail. The moveable portion 300 extends between a first end 302 and a second end 304. The moveable portion 300 also includes a first side 306, a second side 308, a top 310, and a bottom 312. As depicted, the moveable portion 300 includes a threaded hole 314 at the first end 302. The threaded hole 314 extends between the first end 302 and a slot 316 (e.g., a relief slot). As depicted, the moveable portion 300 includes a bar 330. The bar 330 extends generally between the first end 302 and the second end 304. The bar 330 also extends between the first side 306 and the second side 308. The bar 330 extends generally between the bottom 312 of the moveable portion 300 and a top surface 330t of the bar 330. The moveable portion 300 includes a series of pin holes 332. As depicted, the pin holes 332 are included in the bar 330. As depicted, the pin holes 332 include a first pin hole 332a, a second pin hole 332b, a third pin hole 332c, a fourth pin hole 332d, and a fifth pin hole 332e.

The moveable portion 300 includes moveable pins 336. In particular, the moveable pins 336 include a first moveable pin 336a, a second moveable pin 336b, a third moveable pin 336c, a fourth moveable pin 336d, and a fifth moveable pin 336e. The moveable pins 336a-e are mounted in the corresponding pin holes 332a-e. The pins 336 can be straight pins with no shoulders. The mounting of the moveable pins 336 can include pressing the pins 336 into the pin holes 332. The moveable pins 336 extend between a first end 342 and a second end 344. The moveable pins 336 include a diameter 346. In preferred embodiments, the diameter 346 is pressed into the pin hole 332 until the first end 342 is flush (i.e., even) with the bottom 312 of the moveable portion 300.

Turning now to FIGS. 10-14, the adjustment bracket 400 will be described in detail. The adjustment bracket 400 extends between a first end 402 and a second end 404. As depicted, the first end 402 generally corresponds to the first end 32 of the test fixture 30, and the second end 404 generally abuts the first end 102 of the base 100. The adjustment bracket 400 also includes a first side 406, a second side 408, a top 410, and a bottom 412. As depicted, the first side 406 generally corresponds to the first side 36 of the test fixture 30, the second side 408 generally corresponds to the second side 38 of the test fixture 30, the top 410 generally corresponds to the top surface 230t of the plate 230, and the bottom 412 generally corresponds to the bottom 42 of the test fixture 30.

The adjustment bracket 400 includes a hole 414 (i.e., an actuator hole). As depicted, the hole 414 is centered between the first side 406 and the second side 408. The adjustment bracket 400 further includes a counter-bore 416 positioned concentric with the hole 414. The counter-bore 416 opens toward the first end 402 of the adjustment bracket 400. The counter-bore 416 defines a shoulder 418 upon meeting the hole 414. The adjustment bracket 400 further includes a first stacking pin hole 420 and a second stacking pin hole 422. The stacking pin holes 420, 422 open toward the top 410 of the adjustment bracket 400. The adjustment bracket 400 further includes a set of holes 426 (e.g., end holes). In particular, the holes 426 include a first hole 426a, a second hole 426b, a third hole 426c, and a fourth hole 426d. The holes 426 correspond with the holes 126 of the base 100. As depicted, each of the holes 426 includes a countersink 428. The adjustment bracket 400 further includes a pair of stacking holes 430. The stacking holes 430 open toward the bottom 412 of the adjustment bracket 400. The stacking holes 430 are positioned adjacent the first side 406 and the second side 408 of the adjustment bracket 400. Each of the stacking holes 430 includes a hole bottom 432. The adjustment bracket 400 further includes an actuator retainer notch 434. The actuator retainer notch 434 includes a bottom 434b and a pair of walls 434w adjacent each side of the bottom 434b. The adjustment bracket 400 further includes a relief 436. As depicted, the relief 436 is positioned adjacent the top 410 and the second end 404. The relief 436 includes a bottom 436b and a side 436s (see FIG. 14). The bottom 436b generally abuts a portion of the bottom 212 of the stationary portion 200 adjacent the first end 202 of the stationary portion 200. The side 436s generally abuts the first end 202 of the stationary portion 200.

Turning now to FIG. 15, the actuator 500 will be described in detail. As depicted, the actuator 500 is a screw. The actuator 500 extends between a first end 502 and a second end 504. The actuator 500 includes a head 506 positioned at the first end 502. The head 506 includes a diameter 508 and a drive attachment 510. In the depicted embodiment, the drive attachment 510 is a slot (e.g., a screwdriver slot). A reduced diameter portion 512 is positioned adjacent the head 506. A shoulder 514 is defined between the diameter 508 and the diameter 512. The reduced diameter portion 512 includes a groove 516. A bottom of the groove 516 defines a diameter 518. The groove 516 extends between a first wall 520 and a second wall 522. The reduced diameter 512 terminates at a shoulder 524. A threaded portion 526 extends between the shoulder 524 and the second end 504.

Turning now to FIG. 16, the preloading member 540 will be described in detail. As depicted, the preloading member 540 is a wave washer. The preloading member 540 extends between a first side 542 and a second side 544. The preloading member 540 further defines an inner diameter 546 and an outer diameter 548.

Turning now to FIG. 17. The keeper 560 will be described in detail. The keeper 560 extends between a first side 562 and a second side 564 (see FIG. 2). The keeper 560 further includes a first edge 566, a second edge 568, a top 570, and a bottom 572. The keeper 560 includes a slot 574. As depicted, the slot 574 is centered between the first edge 566 and the second edge 568. The slot 574 extends through the bottom 572. A radius 576 is defined at an end of the slot 574.

Turning now to FIGS. 18-20. The support pin assembly 600 will be described in detail. The support pin assembly 600 extends from a top 602 to a bottom 604. As depicted, the support pin assembly 600 includes a support pin 610, a plunger 640, and a spring 680.

The support pin 610 extends from a top 612 to a bottom 614. The support pin 610 defines a pin diameter 616 adjacent to the top 602. As depicted, a radius 618 is defined between the pin diameter 616 and the top 612 of the support pin 610. The support pin 610 includes a flange 620 adjacent the bottom 614. The support pin 610 includes a bore 622 that opens toward the bottom 614. As depicted, the bore 622 is concentric with the pin diameter 616. The bore 622 defines an inner diameter 624. The bore 622 includes a bottom 626. A chamfer 628 is defined between the bore 622 and the bottom 614.

The plunger 640 extends between a first end 642 and a second end 644. The plunger 640 includes a diameter 646 adjacent the first end 642. The plunger 640 includes a flange 648 adjacent the second end 644. In the depicted embodiment, the flange 648 defines a diameter 650. A radius 652 is defined between the diameter 650 and the second end 644. A radius 654 is defined between the diameter 650 and a shoulder 656. The shoulder 656 is positioned between the diameter 646 and the diameter 650. The diameter 646 of the plunger 640 is sized to have a slip fit with the inner diameter 624 of the support pin 610.

The spring 680 extends between a first end 682 and a second end 684. The support pin assembly 600 is assembled by positioning the spring 680 within the bore 622 and abutting the first end 682 of the spring 680 against the bottom 626 of the bore 622. Upon the insertion of the spring 680 into the bore 622, the first end 642 of the plunger 640 is inserted into the bore 622 of the support pin 610. The first end 642 abuts the second end 684 of the spring 680. Upon the insertion of the first end 642 of the plunger 640 into the bore 622, the spring 680 is compressed. The plunger 640 is thereby spring-loaded to extend away from the bottom 614 of the support pin 610.

The assembly and operation of the test fixture 30 will now be described in detail. To assemble the test fixture 30, the moveable portion 300 may be assembled into the channel 118 of the base 100. In particular, the first side 306 and the second side 308 are positioned adjacent the pair of the walls 118w of the channel 118. The bottom 312 of the moveable portion 300 may be positioned adjacent the bottom 118b of the channel 118. The moveable portion 300 is oriented such that the first end 302 is positioned toward the first end 102 of the base 100 and the second end 304 is positioned toward the second end 104 of the base 100. The spacing between the first side 306 and the second side 308 of the moveable portion 300 is sized for a sliding fit between the walls 118w of the channel 118. Thus, the moveable portion 300 forms a moveable slide with respect to the base 100.

The support pin assembly 600 may be inserted into the slots 214, 216 of the stationary portion 200. The support pin assembly 600 is oriented such that the flange 620 is positioned adjacent the bottom 212 of the stationary portion 200. The pin diameter 616 of the support pin assembly 600 protrudes through the slots 214, 216. In the depicted embodiment, there are a total of ten of the slots 214, 216 and there are a total of ten support pin assemblies 600. One support pin assembly 600 is assembled to each of the slots 214, 216. The stationary portion 200, with the support pin assemblies 600 inserted, may be positioned over and attached to the base 100, with the moveable portion 300 inserted. The mounting holes 224 of the stationary portion 200 are aligned with the corresponding holes 124 of the base 100. A set of fasteners 702 may be inserted through the holes 224 and screwed into the holes 124. The stationary portion 200 is thereby attached to the base 100, with the moveable portion 300 and the support pin assemblies 600 trapped between them.

Upon assembling the stationary portion 200 to the base 100, the springs 680 of the support pin assemblies 600 are compressed. The flange 620 of each of the support pin assemblies 600 is thereby held in contact with the bottom 212 of the stationary portion 200. In addition, the second end 644 of the plunger 640 is thereby held in contact with the bottom 114b, 116b of their respective channel 114, 116. The contact between the flange 620 and the plate 230 and the contact between the second end 644 and the bottom 114b, 116b keeps the support pin 610 oriented perpendicular to the top surface 230t of the plate 230. The contact also provides friction that keeps the support pin assembly 600 in place. To move the support pin assembly 600, the support pin 610 can be slid along the slots 214, 216 by overcoming the friction. In certain embodiments, the support pin assembly 600 may be moved by depressing the support pin 610 and thereby further compressing the spring 680. Upon the compression being released between the flange 620 and the bottom 212 of the stationary portion 200, the support pin assembly 600 may be moved along the slots 214, 216. Frictional characteristics of the support pin assembly 600 may be adjusted appropriately to give a desired combination of holding power and moveablility. The spring 680 may be selected to tailor the desired holding power and moveability of the support pin assembly 600.

As the stationary portion 200 is positioned over and fastened to the base 100, the moveable pins 336 are inserted into the slots 218, correspondingly. Upon assembly of the base 100, the stationary portion 200, the moveable portion 300, and the support pin assemblies 600, the moveable portion 300 may be slid along the channel 118, with each of the moveable pins 336 positioned within the slots 218, correspondingly.

To control the position of the moveable portion 300 relative to the stationary portion 200, the actuator 500 may be adjusted and/or set. To install the actuator 500 to the test fixture 30, the actuator 500, the adjustment bracket 400, the preloading member 540, and the keeper 560 may be preassembled. The actuator 500 is first fitted with the preloading member 540. In the depicted embodiment, two of the preloading members 540 are used. The inner diameter 546 of the preloading member 540 is positioned over the diameter 512 of the actuator 500 and positioned adjacent the shoulder 514. The second end 504 of the actuator 500 may now be inserted through the counter-bore 416 and then through the hole 414. The actuator 500 is further slid through the hole 414 until the preloading members 540 become compressed between the shoulder 418 and the shoulder 514. The groove 516 is now positioned in the actuator retainer notch 434. The slot 574 of the keeper 560 is now positioned within the groove 516 straddling the diameter 518.

Upon the keeper 560 being positioned within the groove 516, the actuator 500 is attached to the adjustment bracket 400. However, the actuator 500 is free to rotate within the hole 414. When sliding the keeper 560 in the groove 516, the edges 566, 568 of the keeper 560 are positioned adjacent the walls 434w of the actuator retainer notch 434. Upon assembly, the top 570 of the keeper 560 is preferably positioned adjacent the relief 436 of the adjustment bracket 400. The adjustment bracket 400, with the actuator 500 sub-assembled, may now be attached to the base 100. The relief 436 is positioned adjacent the stationary portion 200. In particular, the first end 202 of the stationary portion 200 overhangs the first end 102 of the base 100. The holes 426 are aligned to the corresponding holes 126 of the base 100. A set of fasteners 700 may be inserted through the holes 426 and threaded into the holes 126. The adjustment bracket 400 is now secured to the test fixture 30. The keeper 560 is trapped between the overhanging portion of the stationary portion 200 and the groove 516 of the actuator 500.

In certain embodiments, the threads 526 of the actuator 500 are engaged with the threaded hole 314 of the moveable portion 300 during the assembly process. In other embodiments, the adjustment bracket 400 may be secured to the base 100 first and then the threads 526 of the actuator 500 may be engaged with the threaded hole 314 of the moveable portion 300. In either case, upon the threads 526 of the actuator 500 engaging the threaded hole 314 of the moveable portion 300, the position of the moveable portion 300 may be controlled by the actuator 500. It should be noted that the preloading member 540 may provide a zero-backlash position to the actuator 500 within the adjustment bracket 400. The threads 526 and the threaded hole 314 may incorporate standard machine threads, ACME profile threads, ball screw threads, or other threads that are known in the art. The threads 526 and the threaded hole 314 may either be threaded right-handed or left-handed. The connection between the threads 526 and the threaded hole 314 may be zero-backlash or low backlash.

As mentioned above, FIGS. 26 and 27 illustrate the testing of one of the specimens 800, 900, respectively. The test fixture 30, as illustrated at the figures, may test between one and five specimens simultaneously. FIG. 28 illustrates the test fixture 30 testing five of the specimens 800 simultaneously. In other embodiments, the test fixture 30 may be able to accommodate additional test specimens simultaneously. The test specimens 800, 900 may be different test specimens in different tests. In preferred embodiments, the test specimens tested by the test fixture 30 in a given test may be identical to each other. In particular, the test specimens in a given test may be made of the same material, and the test specimens in a given test may be of the same thickness.

In the depicted embodiment, the pins 236, 238, 336, and 610 are material engaging components that engage the test specimens 800, 900. As depicted, the material engaging components are material engaging pins. In other embodiments, the material engaging components can take other forms. In the depicted embodiment, the pins 236, 238, 336, and 610 are cantilevered pins with a free end and a supported end. In the depicted embodiment, the free ends of the cantilevered pins are positioned on the same side (e.g., the top) of the test fixture 30, and the supported ends are all positioned on the same side (e.g., the bottom) of the test fixture 30. Having the free ends configured together allows easy loading and unloading of the test specimens 800, 900 from an open side (e.g., the top) of the test fixture 30 with the free ends.

A method of using the test fixture 30 to test the test specimens 800 or 900 will now be described in detail. The test fixture 30 may be initially set at the first configuration 44. The test fixture 30 may be able to accommodate a variety of thicknesses of various test specimens in various test setups. In preferred embodiments, the same thickness of test specimens is used throughout the test fixture 30 in a given test. As depicted, the test specimen 800 has a thickness $T_1$ between a first side 802 and a second side 804 of the test specimen 800. Likewise, the test specimen 900 has a thickness $T_2$ between a first side 902 and a second side 904 of the test specimen 900. In the depicted examples, the thickness $T_1$ is greater than the thickness $T_2$. The range of thicknesses accommodated by the test fixture 30 may be limited by a space $T_M$ between corresponding pins 236, 238 and the corresponding support pin assembly 600 (see FIG. 21). The test specimen may be loaded into the test fixture 30, configured to the first configuration 44, by inserting the test specimen between the pins 236, 238 and the corresponding support pin assembly 600 (e.g., from the open side). One or both of the support pin assemblies 600 may now be slid toward the corresponding pins 236, 238 until the test specimen is sandwiched between them. As depicted, a bottom 812 of the test specimen 800 or a bottom 912 of the test specimen 900 abut the top surface 230t of the plate 230 when the test specimens 800 or 900 are loaded into the test fixture 30. The test specimen 800 extends between a first end 806 and a second end 808. Likewise, the test specimen 900 extends between a first end 906 and a second end 908. A distance between the first ends 806, 906 and the second ends 808, 908 is preferably greater than the distance $D_S$ and includes enough excess length to accommodate the deformed profile of $P_1$, $P_2$ of the test specimens 800, 900.

Upon loading the test specimens 800 or 900 into the test fixture 30, the actuator 500 may be adjusted as desired to impart the desired profile $P_1$, $P_2$ to the test specimens 800, 900. The scale 226 and/or the indicator 228 may give an indication of the configuration of the test fixture 30. In addition, other instruments may be used to determine if the configuration of the test fixture 30 matches the desired configuration and in setting the test fixture 30 to the desired configuration. For example, a measurement may be taken with calipers between a reference surface and one of the moveable pins 336 and/or the moveable portion 300. As illustrated at FIG. 22, a measurement M is taken between the second end 304 of the moveable portion 300 (i.e., the slide) and the second end 34 of the test fixture 30.

The test specimens 800, 900 may have a width that extends generally perpendicular to the top surface 230t of the plate 230. In particular, the test specimen 800 has a width that extends from the bottom 812 to a top 810 of the test specimen 800. Likewise, the test specimen 900 has a width that extends from the bottom 912 to a top 910 of the test specimen 900. In preferred embodiments, the tops 810, 910 of the test specimens 800, 900 are below the top 310 of the moveable portion 300 and the top 210 of the stationary portion 200.

In the depicted embodiment, the test fixture 30 can be stacked on top of another test fixture 30. In this way, multiple test fixtures 30 can be positioned one on top of the other to facilitate multiple tests using multiple test fixtures 30. A pair of the stacking pins 704 are inserted into the first and the second stacking pin holes 220, 222 of the stationary portion 200. Another pair of the stacking pins 704 is inserted into the first and the second stacking pin holes 420, 422 of the adjustment bracket 400. To stack the additional test fixture 30 on the stacking pins 704, the stacking holes 130 of the base 100 and the stacking holes 430 of the adjustment bracket 400 are positioned over free ends of the stacking pins 704. The hole bottoms 132 of the stacking holes 130 and the hole bottoms 432 of the stacking holes 430 come to rest on the free ends of the stacking pins 704.

In certain embodiments, the test fixture 30 may be used in conjunction with other tests (e.g., chemical tests). To accommodate such tests, materials used in the test fixture 30 are preferably compatible and not reactive with components of the other tests. In the depicted embodiment, the test fixture 30 is made of stainless steel materials that resist reaction with certain chemicals. The test fixture 30, along with the test specimens 800 or 900, may be submerged in a tank containing a liquid chemical.

In the present disclosure, references are made to various orientations (e.g., top, bottom, side, etc.). It will be appreciated that these references are not limiting references and that various embodiments of the present disclosure may have some or all of these references reoriented. In the present disclosure, references are made to the mobility of certain components (e.g., stationary, moveable, etc.). It will be appreciated that these references are not limiting references and that various embodiments of the present disclosure may have other mobility for some or all of these components.

Various modifications and alterations of this disclosure will become apparent to those skilled in the art without departing from the scope and spirit of this disclosure, and it should be understood that the scope of this disclosure is not to be unduly limited to the illustrative embodiments set forth herein.

What is claimed is:

1. A test fixture for applying a prescribed displacement to a material, the test fixture comprising:
   a first portion including a first material engaging feature and a first support, the first material engaging feature having a supported end mounted to the first support, the first material engaging feature having a free end spaced from the supported end of the first material engaging feature, the first material engaging feature adapted to engage the material between the supported end and the free end of the first material engaging feature at a first location on the material;

a second portion including a second material engaging feature, a third material engaging feature, and a second support, the second and the third material engaging features each having a supported end mounted to the second support, the second and the third material engaging features spaced from each other by a distance, the second and the third material engaging features each having a free end spaced from the supported ends of the second and the third material engaging features, the second material engaging feature adapted to engage the material between the supported end and the free end of the second material engaging feature at a second location on the material, and the third material engaging feature adapted to engage the material between the supported end and the free end of the third material engaging feature at a third location on the material; and an actuator operably connected between the first support of the first portion and the second support of the second portion, the actuator adapted to configure a relative position between the first material engaging feature and the second and third material engaging features.

2. The test fixture of claim 1, wherein the actuator includes a thread.

3. The test fixture of claim 1, wherein the first, the second, and the third material engaging features each include a pin.

4. The test fixture of claim 3, wherein the pins are parallel to each other.

5. The test fixture of claim 3, wherein the first support includes a bar.

6. The test fixture of claim 5, wherein the second support includes a plate.

7. The test fixture of claim 6, wherein the plate includes a slot and the pin of the first material engaging feature passes through the slot.

8. The test fixture of claim 1, further comprising a first adjustable material support feature adapted to hold the material against the second material engaging feature at the second location on the material.

9. The test fixture of claim 8, further comprising a second adjustable material support feature adapted to hold the material against the third material engaging feature at the third location on the material.

10. The test fixture of claim 9, wherein the first and the second adjustable material support features each include a support pin.

11. The test fixture of claim 10, wherein the support pin includes a bore that receives a plunger and the plunger is adapted to hold the support pin against the material and thereby hold the material against the material engaging features.

12. The test fixture of claim 11, wherein the support pin includes a spring within the bore that biases the plunger outwardly from the support pin.

13. The test fixture of claim 12, wherein the support pin includes a first flange and the plunger includes a second flange.

14. The test fixture of claim 13, wherein the second portion of the test fixture includes a channel that slidably mounts the first and the second flanges and wherein the first and the second flanges compress against the channel to hold the support pin relative to the second portion of the test fixture.

15. The test fixture of claim 1, wherein the first portion is a moveable portion and the second portion is a stationary portion.

16. The test fixture of claim 1, wherein the first location on the material is between the second and the third locations on the material.

17. A test fixture for simultaneously applying prescribed displacements to a plurality of test specimens, the test fixture comprising:
a first portion including a plurality of material engaging features, the material engaging features of the first portion each adapted to engage one of the test specimens at a first location on the test specimen;
a second portion including a plurality of pairs of material engaging features, the pairs of material engaging features of the second portion each adapted to engage one of the test specimens at a second location and a third location on the test specimen, one of the pair of material engaging features adapted to engage the test specimens at the second locations, and another of the pair of material engaging features adapted to engage the test specimens at the third locations; and
an actuator operably connected between the first portion and the second portion, the actuator adapted to configure a relative position between the material engaging features of the first portion and the pairs of material engaging features of the second portion;
wherein the material engaging features each include a pin; and
wherein the pins are cantilevered and include a free end.

18. The test fixture of claim 17, wherein the actuator includes a thread.

19. The test fixture of claim 17, further comprising a plurality of adjustable material support features adapted to hold the test specimens against the pairs of material engaging features at the second and the third locations on the test specimens.

20. The test fixture of claim 17, wherein the first portion is a moveable portion and the second portion is a stationary portion.

21. The test fixture of claim 17, wherein the first location on each of the test specimens is between the second location and the third location on the test specimen.

22. A test fixture for applying a prescribed displacement to a material, the test fixture comprising:
a first portion including a first pin, the first pin adapted to engage the material at a first location on the material;
a second portion including a second pin and a third pin, the second and the third pins spaced from each other by a distance, the second pin adapted to engage the material at a second location on the material, and the third pin adapted to engage the material at a third location on the material;
a first adjustable material support feature adapted to hold the material against the second pin at the second location on the material;
a second adjustable material support feature adapted to hold the material against the third pin at the third location on the material; and
a common actuator operably connected between the first portion and the second portion, the common actuator adapted to configure a relative position between the first pin and the second and third pins.

23. The test fixture of claim 22, wherein the first adjustable material support feature includes a first adjustable pin and the second adjustable material support feature includes a second adjustable pin.

24. A test fixture for applying a prescribed displacement to a material, the test fixture comprising:
a first portion including a first pin, the first pin adapted to engage the material at a first location on the material;
a second portion including a second pin and a third pin, the second and the third pins spaced from each other by a distance, the second pin adapted to engage the material at a second location on the material, and the third pin adapted to engage the material at a third location on the material;

a first adjustable material support feature adapted to hold the material against the second pin at the second location on the material, the first adjustable material support feature including a first adjustable pin;

a second adjustable material support feature adapted to hold the material against the third pin at the third location on the material, the second adjustable material support feature including a second adjustable pin; and an actuator operably connected between the first portion and the second portion, the actuator adapted to configure a relative position between the first pin and the second and third pins;

wherein the first and the second adjustable pins include a bore that receives a plunger and the plunger is adapted to hold the adjustable pins against the material and thereby hold the material against the second and the third pins, respectively.

25. The test fixture of claim 24, wherein the first and the second adjustable pins include a spring within the bore that biases the plunger outwardly from the adjustable pins.

26. The test fixture of claim 25, wherein the adjustable pins include a first flange and the plungers include a second flange.

27. The test fixture of claim 26, wherein the second portion of the test fixture includes a first channel and a second channel that slidably mount the first and the second flanges of the first and the second adjustable pins and their respective plungers, respectively, and wherein the first and the second flanges compress against the respective channels to hold the adjustable pins relative to the second portion of the test fixture.

28. The test fixture of claim 27, wherein the second portion of the test fixture includes a base and a plate and wherein the first and the second channels are positioned between the base and the plate.

29. The test fixture of claim 28, wherein the plate includes a first slot and a second slot and wherein the first and the second adjustable pins protrude through the first and the second slots, respectively.

30. The test fixture of claim 29, wherein the test fixture includes a third channel that slidably mounts the first portion of the test fixture.

31. The test fixture of claim 30, wherein the third channel is also positioned between the base and the plate and the first portion of the test fixture is captured between the base and the plate.

32. The test fixture of claim 31, wherein the plate includes a third slot and wherein the first pin of the first portion protrudes through the third slot.

33. The test fixture of claim 32, wherein the first pin, the first adjustable pin, and the second adjustable pin are all continuously adjustable.

34. A method for testing a strip of material, the method comprising:
    placing the strip of material adjacent a pair of pins;
    positioning a pair of holding pins adjacent the material opposite the pair of pins thereby holding the strip of material adjacent the pair of pins;
    actuating a third pin relative to the pair of pins thereby deforming the material
    wherein the pair of pins and the third pin are all cantilevered from a base of a test fixture.

35. The method of claim 34, wherein the pair of pins is stationary and the third pin is moveable.

36. The method of claim 34, wherein the holding pins are individually positioned.

37. The method of claim 34, wherein the pair of pins are positioned opposite from each other along the strip of material about the third pin.

* * * * *